United States Patent [19]
Bernhardt et al.

[11] Patent Number: 5,931,730
[45] Date of Patent: Aug. 3, 1999

[54] SECURED SANITARY CATHETER

[75] Inventors: Douglas H. Bernhardt, Shorewood; Casimir E. Lawler, Jr, Deephaven, both of Minn.

[73] Assignee: Meat Processing Service Corporation, Minneapolis, Minn.

[21] Appl. No.: 08/870,195

[22] Filed: Jun. 6, 1997

[51] Int. Cl.[6] ............................................. A22B 5/04
[52] U.S. Cl. ........................ 452/65; 452/67; 604/104
[58] Field of Search .................... 450/65, 67, 68, 450/69; 604/104, 179

[56] References Cited

U.S. PATENT DOCUMENTS

| | | |
|---|---|---|
| 3,721,229 | 3/1973 | Panzer . |
| 3,976,080 | 8/1976 | Bornhorst et al. . |
| 5,007,336 | 4/1991 | Bernhardt et al. ........................ 99/487 |
| 5,203,773 | 4/1993 | Green ....................................... 604/104 |
| 5,279,564 | 1/1994 | Taylor ...................................... 604/104 |
| 5,423,745 | 6/1995 | Todd et al. ................................. 604/53 |
| 5,746,716 | 5/1998 | Vigil et al. ................................. 604/97 |
| 5,769,821 | 6/1998 | Abrahamson et al. .................. 604/104 |

*Primary Examiner*—Willis Little
*Attorney, Agent, or Firm*—Vidas, Arrett & Steinkraus, P.A.

[57] ABSTRACT

The present invention relates to a secured sanitary catheter for administration of treatment solution into animals comprising a catheter body with a longitudinal bore and a sanitary vascular securing device attached to the catheter body. The catheter body has a proximal end and a distal end, with the longitudinal bore terminating in an opening at the distal end of the catheter body, for delivery of treatment solution into a vessel of an animal. The sanitary vascular securing device contains a plurality of slots for mechanically and frictionally engaging the vessel at two or more points. The present invention further relates to a method for using the secured sanitary catheter of the present invention.

29 Claims, 2 Drawing Sheets

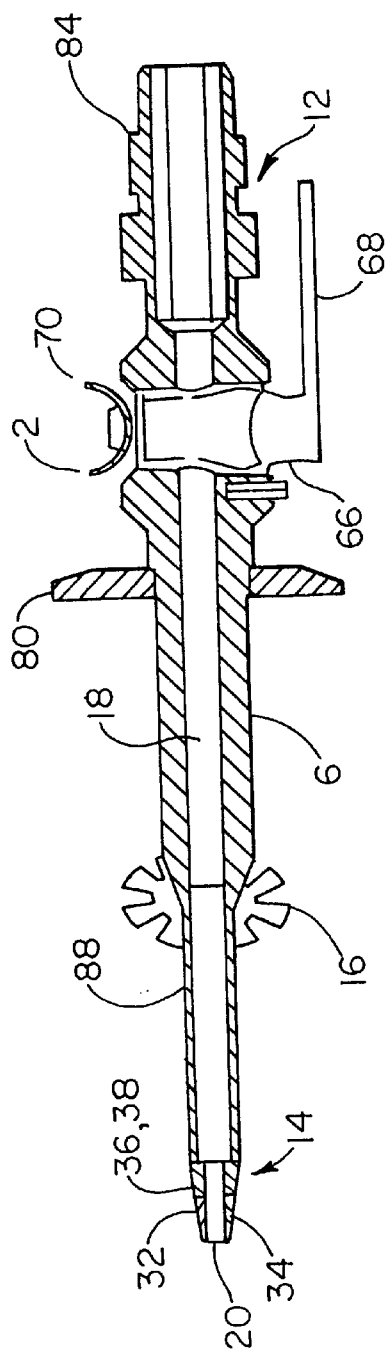
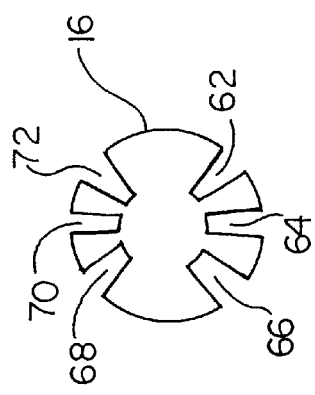
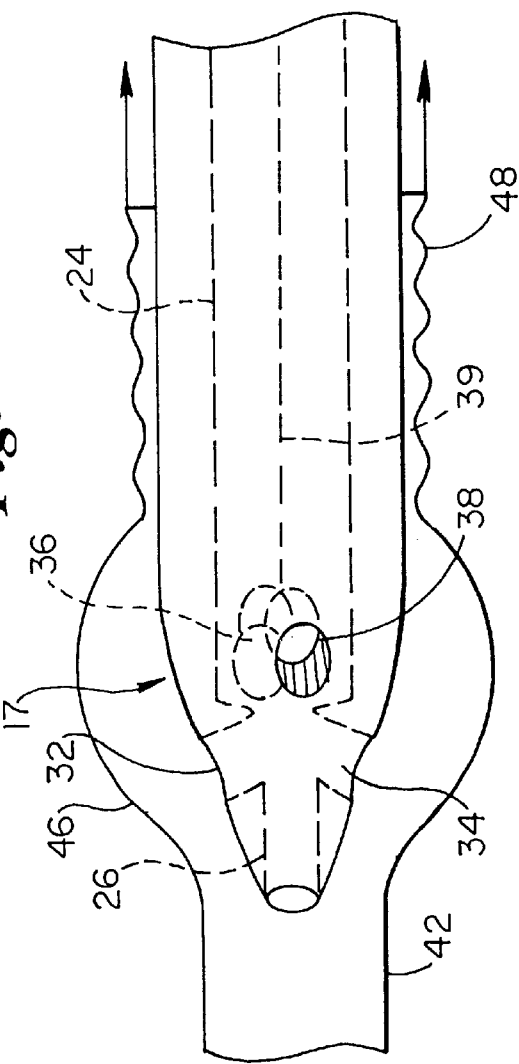

SECURED SANITARY CATHETER

BACKGROUND OF THE INVENTION

The subject invention is related to a slaughtering process apparatus which administers various liquid compositions into the cardiovascular system of animals.

The subject invention is specifically concerned with an apparatus for use in the treatment of animals rapidly, painlessly, and irreversibly approaching death, by administering treatment solution into the animal's circulatory system. The apparatus, as described in U.S. Pat. No. 5,007,336 and incorporated herein by reference, is useful in the treatment of beef, horses, hogs, poultry, deer, buffalo, camel and the like. The apparatus may be portable or permanently located.

When processing an animal, it is necessary to remove the blood from the animal. Because the circulatory system of animals is so convoluted, approximately half the blood of an animal drains unaided during normal bleeding. The blood remaining in the body serves as a source of elements which promotes bacterial growth particularly magnesium, calcium and iron which can also have a deleterious effect in meat. In order to help ensure that all blood is drained from the animal, and to facilitate the treatment of animal muscle, a fluid is typically introduced into the circulatory system of the animal via a catheter or other device through an incision in an artery and the remaining blood rinsed out through a severed vein. It is understood that for the purposes of the present disclosure, the word vessel is intended to include arteries, veins and any other bodily lumen.

Maintaining the sanitation of such devices has been difficult because of the materials used in the construction of such devices, the tendency of the catheters of such devices to become contaminated with air-born and other contaminants, and the tendency of such devices to slip from the animal becoming contaminated with other contaminants from the floor of the processing area.

It is an object of the present invention to provide a sanitary device which provides treatment solution to an animal and which is capable of being securely attached in a sanitary manner to the animal. It is a further object of the present invention to provide a method for the treatment of animals using the apparatus of the present invention.

These and other features of the invention will become apparent from the detailed description provided below.

SUMMARY OF THE INVENTION

The present invention relates to a secured sanitary catheter for administration of treatment solution into animals comprising a catheter body with a longitudinal bore and a sanitary vascular securing device attached to the catheter body. The catheter body has a proximal portion and a distal portion, with the longitudinal bore terminating in a first opening at the distal portion of the catheter body, for delivery of treatment solution into a vessel of an animal. For the purposes of this application, distal shall denote further from the end of the catheter remaining outside the vessel while proximal shall denote closer to the end of the catheter remaining outside the vessel. The sanitary vascular securing device contains a plurality of slots for mechanically and frictionally engaging the vessel at two or more points.

The present invention further pertains to a method of treating animals comprising the steps of providing an animal rapidly, painlessly, and irreversibly approaching death, the animal having a first vessel with a hole therein, and a second vessel comprising an inside portion which is situated within the animal and an outside portion extending outward from the animal, the outside portion having an incision therein, the outside portion in fluid communication with the inside portion, providing a secured sanitary catheter for administration of treatment solution into the second vessel of the animal, the secured sanitary catheter comprising a sanitary vascular securing device containing a plurality of slots for frictionally and mechanically engaging the second vessel and a catheter body, the secured sanitary catheter in fluid communication with a source of treatment fluid, inserting said secured sanitary catheter for administration of treatment solution into the incision, mechanically and frictionally engaging the vessel to the sanitary vascular securing device and allowing the treatment fluid to flow from the treatment fluid source through the apparatus and into the vessel, the fluid draining through the hole. Treatment fluid is allowed to run through the vessels of the animal until the second fluid draining from the hole is largely comprised of the first fluid, the blood having been rinsed from the animal. Finally, the secured sanitary catheter is sanitized prior to reuse.

BRIEF DESCRIPTION OF THE FIGURES

FIG. 1 shows the secured sanitary catheter of the present invention.

FIG. 2 shows an enlargement of the distal end of the secured sanitary catheter of the present invention.

FIG. 3 shows a preferred embodiment of the sanitary vascular securing device

DETAILED DESCRIPTION OF THE INVENTION

Figure 4:
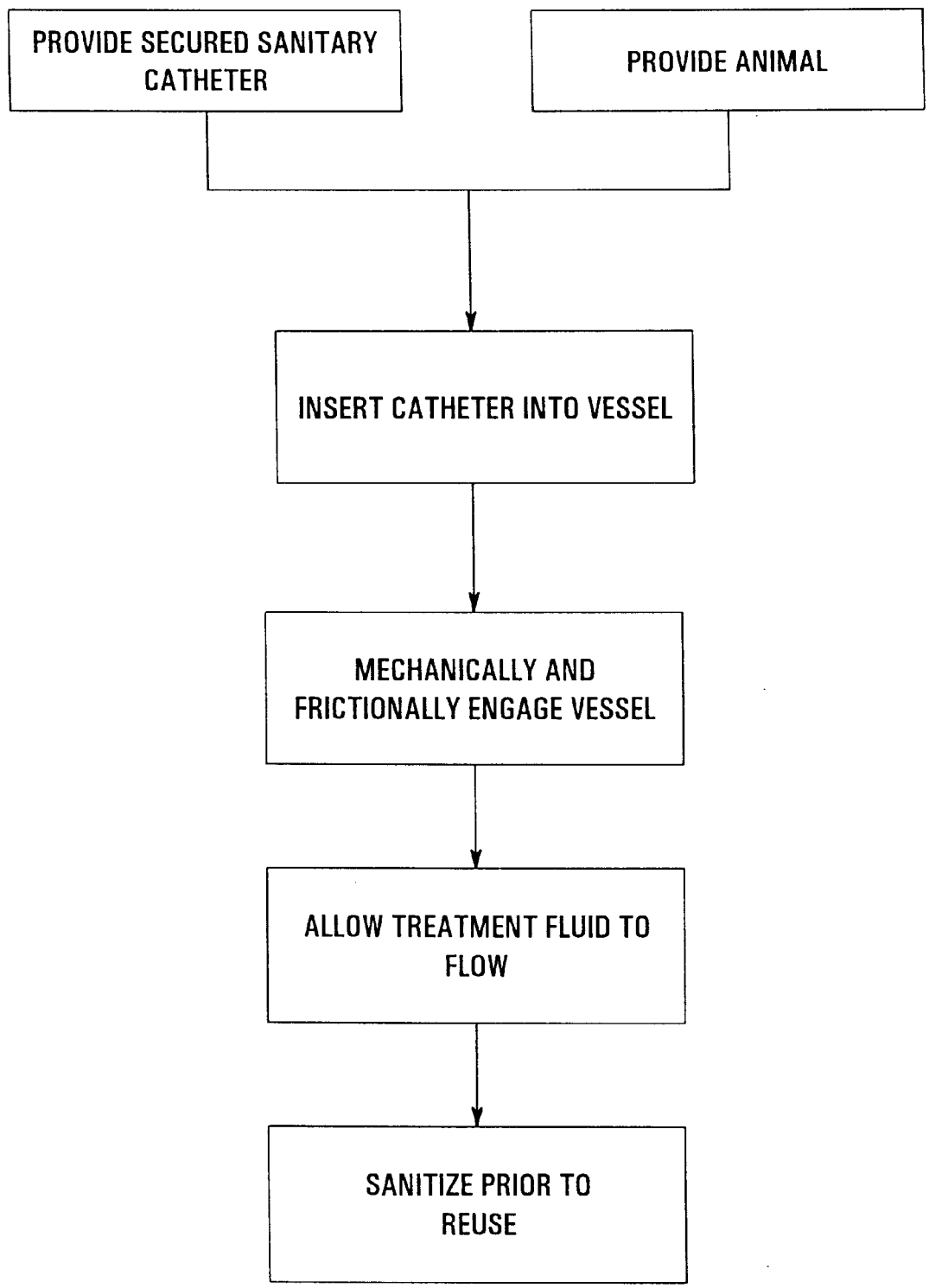
FIG. 4 shows a block diagram of the method of the present application.

Referring to FIG. 1 there is shown a secured sanitary catheter 2 to be described for use in delivering treatment solution into the circulatory system of animals rapidly, painlessly and irreversibly approaching death, which includes a catheter body 6 having proximal 12 and distal 14 ends and a sanitary vascular securing device 16 attached thereto. The distal portion of the catheter body is tapered in part, forming a tapered tip 17 to facilitate insertion of the catheter into a vessel of an animal.

The catheter body has a longitudinal bore 18 extending the length of the catheter and terminating in a first opening 20 at the distal portion of the catheter body, for delivery of treatment solution into a vessel of an animal which rapidly, painlessly, and irreversibly approaching death. The longitudinal bore is characterized by a first diameter along the length of the catheter body extending from the proximal portion of the catheter body to the distal portion of the catheter body, the remaining portion of the bore being characterized by a second diameter, the second diameter being smaller than the first diameter. The region of the bore and catheter body characterized by the first diameter will henceforth be termed the first barrel 24, while the region of the bore and catheter body characterized by the second diameter will henceforth be termed the second barrel 26.

The distal portion of the catheter body is tapered, forming a tapered tip 17 to facilitate insertion into a vessel of the animal. As shown in FIG. 2, the distal portion contains a plurality of additional openings 32, 34, 36 and 38 extending through the tapered tip 17 and in fluid communication with the longitudinal bore 18. The additional openings are angled and sized so as to allow the vessel 42 surrounding the tip of the secured sanitary catheter to be expanded in region 46 by the fluid flow exiting from the sides of the body while simultaneously cinching the vessel in region 48 around the secured sanitary catheter at the most proximal point of the artery on the barrel.

The openings are all of a size 0.25 inches or smaller, the maximum allowable size under the company's Hazard Analysis Critical Control Point Program (HACCP program), although larger sizes up to 0.5 inches could be used should the company's HACCP program size standards increase. It should be noted that the size referred to is either the diameter of the opening in the case of a circular opening or else the length of the long axis of any non-circular opening such as an elliptical opening.

In the preferred embodiment, the catheter body has four such additional openings, two 32, 34 of which are located opposite one another at the distal portion of the tapered tip of the distal portion of the catheter body, the remaining two 36, 38 located in the proximal most portion of the distal tapered tip 17 opposite one another and the pair rotated axially by ninety degrees relative to the first two openings. Other embodiments, however, may have fewer or more than four additional openings of equal or unequal size along the secured sanitary catheter body. The plurality of openings 32 and 34 will be at oblique angles to the longitudinal axis 39 of the catheter body, such that the most distal part of each of the plurality of openings is closer to the longitudinal axis than the most proximal part of the openings. Preferably, the angles will be between 30° and 60° and more preferably, about 45° as depicted in FIG. 2.

While the catheter body may be made of any smooth material that can easily be maintained in a sanitary condition, such as Delrin, Teflon or other USDA approved materials that can be molded, it is preferred to use stainless steel. The tapered tip 17 is highly polished to facilitate insertion into the vessel.

In order to secure the vessel to the secured sanitary catheter, the catheter body comprises a sanitary vascular securing device 16 having proximal and distal ends. The sanitary vascular securing device is mounted on the catheter body, preferably by a small round rod and welded into place. The round rod may also be use to further secure the vessel to the catheter. Alternatively, the sanitary vascular securing device may be formed as an integral part of the catheter body. The catheter body is tapered at or near the vascular securing device, the catheter body having a larger diameter on the proximal side than on the distal side of the taper.

While the sanitary vascular securing device may be any structure to which the vessel can be secured, such as a rod flared outward at one end, preferably the sanitary vascular securing device contains a plurality of slots for mechanically and frictionally engaging the vessel at two or more points. Most preferably, the sanitary vascular securing device 16 will have six slots 62, 64,66, 68, 70 and 72 as shown in FIG. 3. While the sanitary vascular securing device may have slots of only one size, it is desirable for the sanitary vascular securing device to have slots of several sizes so as to accommodate vessels of varying sizes. In order to better secure the vessel to the sanitary vascular securing device and to prevent damage to the vessel, the slots are beveled. While the shape of the sanitary vascular device is round in the preferred embodiment, materials of other shapes containing slots therein, such as, but not limited to, ellipses and squares may be used as well.

The sanitary vascular securing device may be made of any material that can be readily maintained in a sanitary condition such as Delrin, Teflon or other USDA approved materials that can be molded. Preferably, however, stainless steel will be used.

The secured sanitary catheter of the present invention further comprises a stopcock 66 to allow for control of fluid flow through the catheter and into the vessel. Preferably, the stopcock is made of stainless steel which is covered with USDA approved Delrin although other materials such as Teflon, that can be maintained in a sanitary condition may be used as well. To facilitate maintaining the catheter in sanitary form, the stopcock has no threads, surfaces or junctions to which contaminants can attach. In the preferred embodiment, the stopcock is opened and closed by a lever 68 opening away from the distal end of the secured sanitary catheter. The stopcock may be affixed to the catheter body by any sanitary means including a wing nut 70.

The body of the catheter is preferably tapered proximal and distal to the stopcock, the diameter of the catheter body in the region of the stopcock greater than the diameter of the catheter body proximal or distal to the stopcock. This is to allow the stopcock to have maximum surface area to control the starting and stopping of the flow of the treatment liquid and to reduce the overall weight of the secured sanitary catheter.

The secured sanitary catheter of the present invention may, optionally, further comprise a drip guard 80 mounted on the catheter body or formed as an integral of the catheter body. The dripguard functions as a physical barrier between the technician's hand and and the vessel preventing any direct contamination. The dripguard further serves to prevent contamination from the dripping of any condensation that forms on the hose conveying the treatment fluid to the secured sanitary catheter and any air-borne fecal contamination from the hide of the animal that may be contained with the condensation.

The secured sanitary catheter is in fluid communication with a source treatment fluid. The fluid may be delivered by any known sanitary means. In the preferred embodiment, the fluid will be delivered via a sanitary hose attached to the catheter body with a sanitary coupling means 84 known in the art.

Finally, the catheter body has a variety of finishes along different portions of the body. A portion of the first barrel 88, extending from the most distal portion of the first barrel past the sanitary vascular securing device to a point approximately half way to three quarters of the way, preferably approximately two thirds the way to the drip guard has a satin finish to facilitate frictional engagement between the catheter and a vessel. All remaining portions of the first barrel are highly polished to facilitate sanitation. The tapered tip of the catheter body is also highly polished, to facilitate insertion of the catheter into a vessel.

The procedure for using the secured sanitary catheter of the present invention shown in FIG. 4 begins with an animal which is rapidly, painlessly, and irreversibly approaching death, and which is being bleed in any manner prepared by the plant. The prepared bleeding method is a jugular stick. Otherwise, in other techniques, a hole is made in some other suitable vessel of the intact animal. The animal may then be laid on a work surface with its legs extending upwardly or it may be hanging or otherwise suitably positioned. The animal may be moving on a rail or other transporting device.

A portion of a vessel, such as the carotid artery, into which the secured sanitary catheter will be inserted is exposed in the body of the animal. In exposing the vessel, care must be taken to ensure that the vessel remains intact and is not severed. While the carotid artery is the preferred vessel for insertion of the secured sanitary catheter, other vessels such as, but not limited to, the brachial and femoral arteries may be used as well. An incision is made in the exposed portion of the vessel. The incision must be made close enough to the head of the animal to allow for a sufficient length of vessel to secure to the sanitary vascular securing device.

Upon insertion of the catheter into the incision, fluid is allowed to begin to flow from the catheter into the vessel. As fluid begins to flow into the vessel, the catheter is inserted further into the vessel up to the taper at or near the sanitary vascular securing device. Thereafter, the section of vessel exposed from the animal is secured to the sanitary vascular securing device by winding the vessel through the slots. In the case of a slotless sanitary vascular device, such as a rod flared at one end, the vessel must be wound around the rod. While a variety of winding patterns will work, in the very least it is preferable to wind the vessel through one slot of the sanitary vascular securing device thereby changing direction. It is most preferable to wind the vessel through the slots in such a way as to cause the vessel to change direction two or more times. Preferably, if two slots are used, the two slots will be chosen opposite one another. After the winding is completed, the elastic nature of the vessel will result in the secured sanitary catheter being drawn back into the body of the animal.

The secured sanitary catheter is then sanitized prior to insertion into another animal using any method known in the art.

The secured sanitary catheter, being in fluid communication with a source of treatment solution allows treatment solution to be pumped from the source, through the secured sanitary catheter and into the animal's circulatory system. The solution, after rinsing out residual blood, drains from the circulatory system. In a preferred embodiment, treatment solution is allowed to rinse through the vessels of the animal until the fluid draining from the hole is largely free of blood and comprised of the treatment solution. In practice, this treatment method takes approximately two minutes to complete and uses an amount of treatment fluid approximately equal to ten percent of the animal's body weight, although the method can be of longer or shorter duration using more or less fluid.

It is to be understood that this invention is capable of using any of a variety of treatment solutions described in the art. In particular, it is desirable to use a chilled treatment solution capable of lowering the pH of the animal to its ideal level, the solution further possessing anti-microbial characteristics.

While this invention may be embodied in many different forms, there are described in detail herein specific preferred embodiments of the invention. This description is an exemplification of the principles of the invention and is not intended to limit the invention to the particular embodiments illustrated.

What is claimed is as follows:

1. A secured sanitary catheter for administration of treatment solution into animals comprising:
   a catheter body with a longitudinal bore, the catheter body having a proximal portion and a distal portion, the distal portion terminating in a tip sized for insertion into an opening in a vessel of an animal, the tip having a first opening therein, the longitudinal bore terminating in the first opening in the tip, for delivery of treatment solution into a vessel of an animal; and
   a sanitary vascular securing device attached to the catheter body for mechanically and frictionally engaging the vessel at two or more points, the securing device sized larger than the vessel opening.

2. The catheter of claim 1 wherein the catheter body is tapered at or near the sanitary vascular securing device, the diameter of the catheter body being greater proximal to the sanitary vascular securing device than the diameter of the catheter body distal to the sanitary vascular securing device.

3. A secured sanitary catheter for administration of treatment solution into animals comprising:
   a catheter body with a longitudinal bore, the catheter body having a proximal portion and a distal portion, the longitudinal bore terminating in a first opening at the distal portion of the catheter body, for delivery of treatment solution into a vessel of an animal; and
   a sanitary vascular securing device attached to the catheter body for mechanically and frictionally engaging the vessel at two or more points,
the catheter body tapered at or near the sanitary vascular securing device, the diameter of the catheter body being greater proximal to the sanitary vascular securing device than the diameter of the catheter body distal to the sanitary vascular securing device
   wherein the sanitary vascular securing device contains a plurality of slots cut therein and the vessel is wound through at least two slots.

4. The catheter of claim 3 wherein said slots are beveled.

5. The catheter of claim 4 wherein said sanitary vascular securing device is made of stainless steel.

6. The catheter of claim 5 wherein said sanitary vascular securing device is round and contains six slots, the first two slots located substantially opposite each other, the third and fourth slots located substantially opposite each other and rotated forty five degrees relative to the first two slots, the fifth and sixth slots located substantially opposite each other and rotated ninety degrees relative to the first two slots, the first and second slots characterized by a first width, the third, fourth, fifth and sixth slots characterized by a second width, wider than the first width.

7. The catheter of claim 5 wherein the distal portion of the catheter body comprises a tapered tip the tapered tip containing at a plurality of openings extending through the catheter body and in fluid communication with the longitudinal bore.

8. The catheter of claim 7 wherein the catheter body is comprised of a first barrel, the first barrel having distal and proximal ends, in which the longitudinal bore is characterized by a first diameter and a second barrel distal to the first barrel in which the bore is characterized by a second diameter, the second diameter being smaller than the first diameter.

9. The catheter of claim 8 wherein the first opening and the plurality of openings are of a size 0.25 inch or less.

10. The catheter of claim 8 wherein the plurality of openings comprises second, third, fourth and fifth openings extending through the catheter body and in fluid communication with the longitudinal bore.

11. The catheter of claim 10 wherein the second and third openings extend through the tapered tip, the second and third openings located substantially opposite one another.

12. The catheter of claim 11 wherein the fourth and fifth openings extend through the catheter body at the most distal portion of the tapered tip, the fourth and fifth openings located substantially opposite one another, the fourth and fifth openings rotated axially by ninety degrees relative to the second and third openings.

13. The catheter of claim 8 further comprising a drip guard, wherein the drip guard is mounted to the catheter body.

14. The catheter of claim 13 wherein the catheter body further comprises a stopcock.

15. The catheter of claim 14 wherein the catheter body is made of highly polished stainless steel.

16. The catheter of claim 15 wherein the stopcock is made of stainless steel and covered with USDA approved Delrin.

17. The catheter of claim 16 wherein the stopcock has no threads.

18. The catheter of claim 16 wherein the catheter body is tapered proximal and distal to the stopcock, the diameter of the catheter body being larger in the region of the stopcock.

19. The catheter of claim 15 wherein a portion of the first barrel extending from the distal end of the first barrel to a point about two thirds of the way to the drip guard has a satin finish to facilitate frictional engagement between the catheter and a vessel.

20. The catheter of claim 19 wherein the tapered tip is highly polished to facilitate insertion of the catheter into a vessel.

21. The catheter of claim 19 wherein the remainder of the first barrel is highly polished to facilitate sanitation.

22. A method for the treatment of animals comprising the steps of:
providing an animal rapidly, painlessly, and irreversibly approaching death, the animal having a first vessel with an hole therein, and a second vessel comprising an inside portion which is situated within the animal and an outside portion extending outward from the animal, the outside portion having an incision therein, the outside portion in fluid communication with the inside portion,
providing a secured sanitary catheter for administration of treatment solution into the second vessel of the animal, the secured sanitary catheter comprising a sanitary vascular securing device which frictionally and mechanically engages the first vessel, and a catheter body, the secured sanitary catheter in fluid communication with a source of treatment fluid;
inserting said secured sanitary catheter for administration of treatment solution into the incision;
mechanically and frictionally engaging the vessel to the sanitary vascular securing device;
allowing the treatment fluid to flow from the treatment fluid source through the apparatus and into the vessel, a second fluid draining through the hole, until the second fluid is largely comprised of the first fluid and largely free of animal blood; and
sanitizing the secured sanitary catheter prior to reuse.

23. The method of claim 22 wherein the sanitary vascular securing device contains one or more slots for frictionally and mechanically engaging the vessel.

24. The method of claim 22 wherein the animal is moving on a rail.

25. A secured sanitary catheter for administration of treatment solution into animals comprising:

a catheter body with a longitudinal bore, the catheter body having a proximal portion and a distal portion, the longitudinal bore terminating in a first opening at the distal portion of the catheter body, for delivery of treatment solution into a vessel of an animal, the distal portion of the catheter body comprising a tapered tip, the tapered tip containing a plurality of openings extending through the catheter body and in fluid communication with the longitudinal bore, the plurality of openings being constructed and arranged to expand the vessel wall surrounding the distal portion of the secured sanitary catheter by the flow of treatment liquid exiting from the plurality of openings and simultaneously cinching the vessel around the secured sanitary catheter which is proximal of the plurality of openings; and
a sanitary vascular securing device attached to the catheter body for mechanically and frictionally engaging the vessel at two or more points, the sanitary vascular device immovable relative to the catheter body.

26. A secured sanitary catheter for administration of treatment solution into animals comprising:
a catheter body with a longitudinal bore, the catheter body having a proximal portion and a distal portion, the longitudinal bore terminating in a first opening at the distal portion of the catheter body, for delivery of treatment solution into a vessel of an animal, the distal portion of the catheter body comprising a tapered tip, the tapered tip containing a plurality of openings extending through the catheter body and in fluid communication with the longitudinal bore,
the plurality of openings being constructed and arranged to expand the vessel wall surrounding the distal portion of the secured sanitary catheter by the flow of treatment liquid exiting from the plurality of openings and simultaneously cinching the vessel around the secured sanitary catheter which is proximal of the plurality of openings; and
a sanitary vascular securing device attached to the catheter body, containing at least two slots for mechanically and frictionally engaging the vessel at two or more points.

27. A secured sanitary catheter for administration of treatment solution into animals comprising:
a catheter body with a longitudinal bore, the catheter body having a proximal portion and a distal portion, the longitudinal bore terminating in a first opening at the distal portion of the catheter body, for delivery of treatment solution into a vessel of an animal; and
a sanitary vascular securing device attached to the catheter body for mechanically and frictionally engaging the vessel at two or more points,
the catheter body tapered at or near the sanitary vascular securing device, the diameter of the catheter body being greater proximal to the sanitary vascular securing device than the diameter of the catheter body distal to the sanitary vascular securing device
wherein the sanitary vascular securing device consists of a rod attached to the catheter body which mechanically and frictionally engages the vessel at two or more points.

28. A secured sanitary catheter for administration of treatment solution into animals comprising:
a catheter body with a longitudinal bore, the catheter body having a proximal portion and a distal portion, the longitudinal bore terminating in a first opening at the distal portion of the catheter body, for delivery of treatment solution into a vessel of an animal; and a sanitary vascular securing device attached to the catheter body for engaging the vessel at two or more points, wherein the sanitary vascular securing device contains a plurality of slots cut therein.

29. A secured sanitary catheter for administration of treatment solution into animals comprising:

a catheter body with a longitudinal bore, the catheter body having a proximal portion and a distal portion, the distal portion terminating in a tapered tip sized for insertion into an opening in a vessel of an animal, the tip having a plurality of openings therein including pairs of oppositely disposed openings, each opening disposed at an oblique angle relative to the longitudinal axis of the catheter body, the longitudinal bore in fluid communication with each of the openings in the tip, for delivery of treatment solution into a vessel of an animal; and a sanitary vascular securing device attached to the catheter body for mechanically and frictionally engaging the vessel at two or more points.

* * * * *